United States Patent [19]
Gerrone

[11] Patent Number: 5,458,640
[45] Date of Patent: Oct. 17, 1995

[54] CANNULA VALVE AND SEAL SYSTEM

[76] Inventor: Carmen J. Gerrone, 110 Dunkard Church Rd., Stockton, N.J. 08559

[21] Appl. No.: 238,475

[22] Filed: May 5, 1994

Related U.S. Application Data

[63] Continuation-in-part of Ser. No. 10,769, Jan. 29, 1993, Pat. No. 5,312,351, and a continuation-in-part of Ser. No. 42,488, Apr. 2, 1993, Pat. No. 5,320,608.

[51] Int. Cl.$^6$ ............................. A61M 5/178; A61M 5/00; A61M 25/00
[52] U.S. Cl. ............................. 604/264; 604/158; 604/249
[58] Field of Search ............................. 604/158, 161, 604/164, 167, 246, 247, 249, 256, 264, 905

[56] References Cited

U.S. PATENT DOCUMENTS

| | | | |
|---|---|---|---|
| 4,781,702 | 11/1988 | Herrli | 604/905 |
| 4,917,668 | 4/1990 | Haindl | 604/167 |
| 4,935,010 | 6/1990 | Cox et al. | 604/167 |
| 5,156,596 | 10/1992 | Balbierz et al. | 604/167 |
| 5,322,518 | 6/1994 | Schneider et al. | 604/167 |
| 5,330,437 | 7/1994 | Durman | 604/167 |
| 5,350,393 | 9/1994 | Yoon | 604/167 |
| 5,354,280 | 10/1994 | Haber et al. | 604/167 |

*Primary Examiner*—C. Fred Rosenbaum
*Assistant Examiner*—Frank Wilkens, III
*Attorney, Agent, or Firm*—Richard C. Woodbridge

[57] ABSTRACT

A surgical cannula includes a first valve seal for preventing insufflation gas from escaping from a patient's abdomen when an instrument is inserted or removed through the cannula. The valve seal has a V-shaped cross section and includes two opposing lips which face each other across a slit. Each lip has an internal and external edge separated by an intermediate section. The front surface of the first seal is relatively flat and has a width X. The preferred distance between the internal and external edges is preferably one-half X. This permits the internal edges to absorb the shock and damage from the introduction of a sharp instrument such as a trocar into the cannula without destroying the sealing capability of the external edges. A spring-loaded tubular member is located within the cannula housing and a reducer subassembly and is normally biased away from the interior surface of the first seal. When an instrument is introduced into the tubular member, it opens the first seal in such a way as to avoid damage to the first seal and, further, permits the withdrawal of tissues without interference. A second fixed or permanent seal located at the rear end of the tubular means also helps to prevent gas loss. Moreover, a plurality of interchangeable end seals can be selectively attached to the end of the instrument. The end seals provide opening apertures that match instruments, such as trocars, having various different outside diameters.

10 Claims, 11 Drawing Sheets

FIG. 14

CANNULA VALVE AND SEAL SYSTEM

CROSS REFERENCES TO RELATED APPLICATIONS

This application is a continuation in part of my U.S. patent application Ser. No. 08/010,769 filed on Jan. 29, 1993 now U.S. Pat. No. 5,312,351 and entitled, "Combined Pneumo-Needle and Trocar Apparatus" and my U.S. patent application Ser. No. 08/042,488 filed on Apr. 2, 1993 now U.S. Pat. No. 5,320,608 and entitled, "Combined Pneumo-Needle and Trocar Apparatus." The entire contents of both co-pending applications are hereby incorporated by reference into this disclosure.

BACKGROUND OF THE INVENTION

1. Field of the Invention

This invention relates to medical instruments and, in particular, to a cannula valve and seal system for use with an instrument such as a trocar.

2. Description of Related Art

During the performance of laparoscopic surgery, it is not uncommon to use as many as five trocars in a single procedure in order to advance operating instruments into the abdominal cavity of a patient. The valving system employed with the cannula that holds and guides the trocar is very important. First, the valving system must prevent the loss of insufflation gas leaking out of the abdominal cavity whether or not instruments are present within the cannula lumen. Second, the valving system must pose little or no resistance to the advancing of instruments or the withdrawal of tissues through the valving system. Third, given the fact that many different trocars of varying outside diameters are available for use and because space is limited around the operating table, it is desirable that the trocars be operatable using just one hand. In particular, it is desirable that only one hand be necessary to advance the instrument into the patient and to withdraw the instrument with tissues on it without stripping the tissues off or causing the tissues to hang up in the valve and seal system.

In the prior art, it was common to seal off gas leaks by using a two-component valve employing a gasket/seal arrangement. The first valve is typically located in the cannula housing and seals when the trocar or other instrument is not present. A second gasket/seal, which is removable and exchangeable and sized for instruments of varying diameters, is located proximally with respect to the first seal thereby sealing the cannula as the trocar is introduced into it or removed from it. One of the major problems with such prior art systems is that they require two hands for operation and do not satisfactorily seal the cannula from the loss of insufflation gas.

For example, U.S. Pat. Nos. 4,654,030; 4,931,042; and 5,030,206, describe a swinger flapper valve that swings closed when instruments are not present and a gasket/seal located proximally to the valve to seal the lumen when instruments are present.

U.S. Pat. Nos. 4,535,773 and 4,972,827 describe a trumpet type valve or slide valve which is spring-loaded to close the lumen when instruments are not present and includes a gasket/seal similarly located proximally to seal the lumen when instruments are present. These devices and others currently known in the prior art typically require a manual movement and the use of two hands to open and close the valve. Additionally, this prior art is mechanically more complicated, and thereby more costly and more difficult to clean when re-sterilization and reuse are intended. They do not provide for the easy passage of irregularly shaped instruments, and most importantly, are not adapted for the easy passage of tissue. Further, the changing of seal/gaskets is cumbersome, and because they are separate components, they become loose making them difficult to account for during use.

There have been several attempts to solve such problems in the prior art. Several devices use commercial duckbill-type check valves such as described in U.S. Pat. No. 5,010,925 and similar to those commonly used in automotive, appliance, medical and specialty applications. Such prior art duckbill valves are slit at one end to create one set of converging lips. While these prior art valves are effective for liquids and gases, they are not effective for use in laparoscopic surgical procedures because they do not allow for the easy withdrawal of tissues. Sample tissue is easily dislodged from devices grasping them as strong resistance from the valve is encountered during the withdrawal process. Occasionally, the resistance is large enough to cause the unintended withdrawal of the cannula from the patient's abdominal cavity.

U.S. Pat. No. 4,960,412 describes the application of a duckbill valve having a concave design but differing from other prior art designs in that bosses on the valve acting on inner surfaces of the valve holding chamber, rather than gas pressure, keep the valve closed. This type of valve would be particularly adverse to passing tissue in the opposite direction because the opposing bosses, designed for the purpose of maintaining closure of the lips by blood pressure, is contrary to the concept of allowing easy passage of tissues or irregularly shaped instruments that can "hang up" or "catch on" the valve and be difficult to remove.

U.S. Pat. No. 5,122,122 describes a duckbill valve having a spherical design. The lips have a deliberately thin design, which causes them to fold back on themselves, thereby turning inside out. They exhibit unacceptably high withdrawal resistance and further are not able to adequately seal. Additionally, due to the delicate nature of the lip edge, the valves are easily damaged by tears and/or cuts made by sharp instruments passing through them. This wear ultimately makes the valve difficult to seal.

U.S. Pat. No. 5,242,412 describes a valve having converging sealing lips which generally operates according to the principles of commercially available duckbill valves such as described in U.S. Pat. No. 5,010,925. This includes internal converging walls and an associated slit which terminates at the apex of a "V". It creates one set of delicate valve lips which are easily damaged. Further, they are not conducive to passing tissues and instruments through without high forces of resistance. When all is considered, it exhibits the same disadvantages common with all the prior art designs. Further, by nature of the valve design, additional diverging lip extensions are needed to prevent the inward collapse of the sealing lips. It appears that the lip extensions could potentially interfere with consistent, reliable valve closure.

Finally, the prior art does not disclose valves which are easily removable and/or replaceable as required in reusable device applications.

SUMMARY OF THE INVENTION

Briefly described, the invention comprises a surgical apparatus that efficiently prevents the leakage of gas from a patient's abdominal cavity. It substantially eliminates resistance as instruments and tissues are withdrawn through it. It can also be automatically operated with one hand or can be manually operated as well.

The invention includes three embodiments of a cannula subassembly. Each embodiment includes a converging lip valve seal which is universal to trocars and instruments ranging in size from 3 mm to 12 mm in diameter. The invention further comprises a reducer subassembly having a fixed seal means and an attachment means to remove and replace interchangeable end seals sized for instruments of varying outside diameters. The separability of the cannula and reducer subassemblies make it possible to discard the disposable reducer subassembly and to replace the converging lip valve seal when the cannula subassembly is to be resterilized between operative procedures.

Several receptacle or storage stations located either on the reducer or cannula subassemblies provide a means to attach and manage otherwise loose interchangeable end seals when smaller or larger instruments are needed. After use, rather than removing them from the field which requires extra accountable management, they are attached to the receptacle stations. This provides for accountable, safe and convenient storage of the seals which remain in a standby position for reuse or are discarded when the surgical procedure has been completed.

The converging lip valve seal is preferably made of a flexible, resilient material with high tear resistance. It has high lubricity characteristics which can be further enhanced with a silicone lubricant coating to reduce frictional resistance of instruments. The valve has a circular cross section at its proximal end and thereafter progresses to a "V" or "chisel" shaped cross section towards its distal end such that the inside lumen provides a large pathway for easy access with minimal interference due to stiffness. This maintains the distal extension of the lip edges so they do not fold back inside out. The outside surface of the "V" cross section is such that when instruments are not present, abdominal pressure acting on the "V", closes the converging lips sealing the lumen. The "V" cross section is truncated at its distal end thereby creating a transverse leading front surface of width "X" perpendicular to the central axis of the seal. When the end is slit, each opposing face has a set of lip internal and external edges separated by a width of approximately ½ X. In contrast, prior art valves normally comprise just one set of lip edges. The internal lip edges of the present invention absorb cuts and/or tears from sharp devices entering and passing through into the abdominal cavity. The internal lip edges move the external lip edges out of the path of the leading points of sharp instruments such as trocars thereby avoiding damage to the external lip edges.

In the preferred embodiment of the invention, a spring-loaded tubular structure acts in a dual role to either automatically or manually open and close the valve seal. In the automatic mode, as force from withdrawal of tissue and instruments is felt by the converging lips of the valve, a spring is compressed and the valve automatically moves outward. The valve lips pass over an interior tubular structure thereby opening the valve. The tubular structure then becomes the pathway out of the cavity thereby eliminating resistance to withdrawal. When the force is removed after withdrawal, the spring returns the valve to its original position away from the tubular structure thereby closing the valve seal.

When it is desired to manually open the valve, this can be accomplished by manually pushing the tubular structure inward. This compresses the spring, and the tube then passes into and through the converging valve lips, opening them and thereby creating a non-interfering pathway into the abdominal cavity. It simultaneously desuflates or evacuates the cavity of smoke when present, and also acts to move the converging valve lips away from contact with sharp instruments that would otherwise damage the lips and render them unsealable. When the tubular structure is manually released, the spring returns the tubular structure to its original position thereby closing the valve.

In a second embodiment of the invention, a tubular structure is located concentrically in a fixed relationship with respect to the internal walls of the "V" shape of the converging lip valve seal such that when tissues or instruments are withdrawn, the tube does not allow the lips to fold inward. The lips in this position are supported by the tube which then becomes the pathway in and out and which results in a lower force of resistance to instruments during withdrawal.

In a third embodiment, in which there is no tubular structure present, the reducer subassembly comprises a fixed seal means and an attachment means for interchangeable end seal means of varying diameters. It also includes a receptacle for storage of the interchangeable end seal means.

These and other features of the invention will be more fully understood by reference to the following drawings.

DETAILED DESCRIPTION OF THE PREFERRED EMBODIMENT OF THE INVENTION

During the course of this description, like numbers will be used to identify like elements according to the different views that illustrate the invention.

Figures 1, 2, 3:
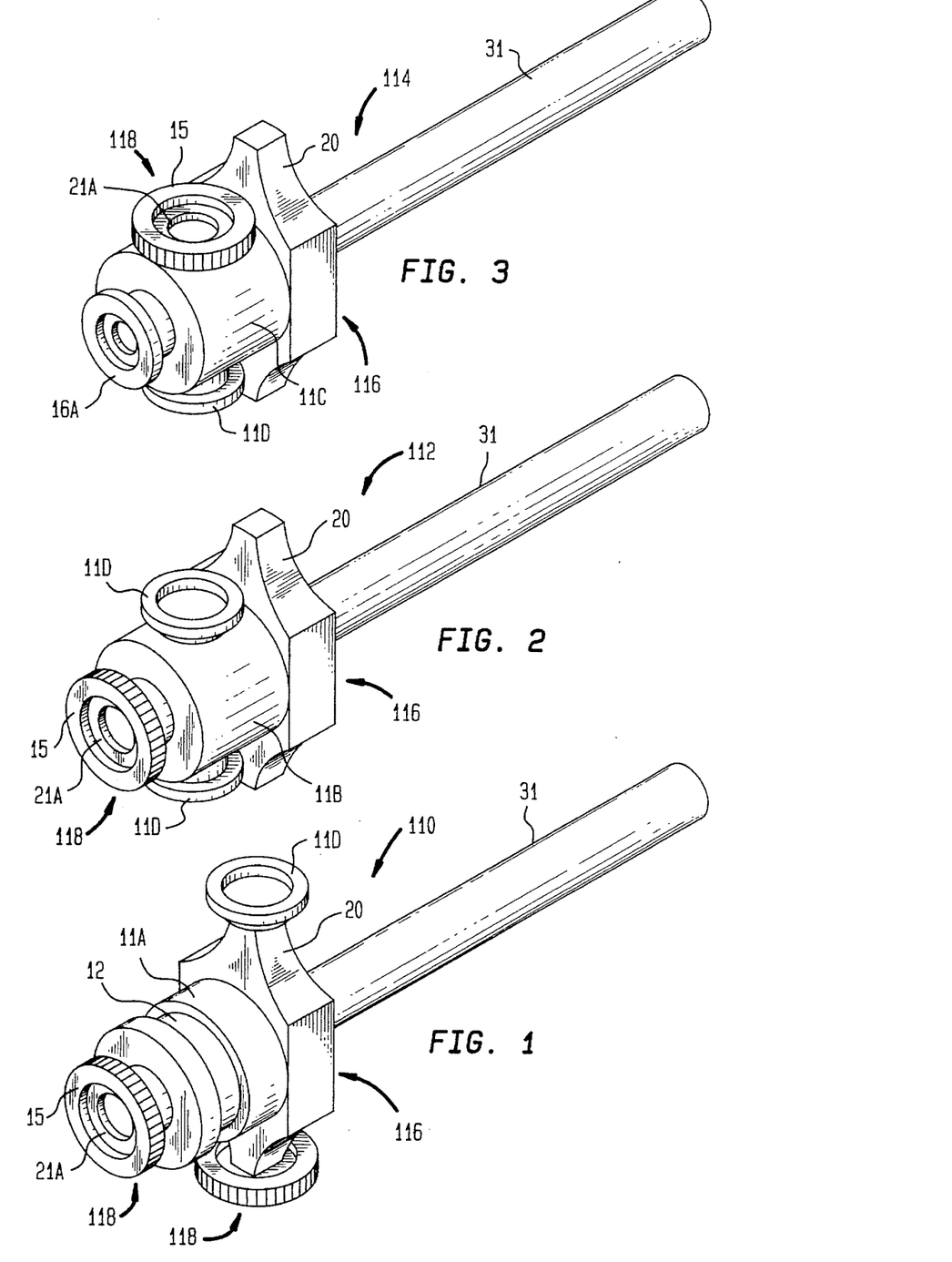
FIG. 1 is a perspective view of the assembled cannula and reducer subassemblies according to the preferred embodiment of the invention.
FIG. 2 is a perspective view of the assembled cannula and reducer subassemblies according to a second embodiment of the invention.
FIG. 3 is a perspective view of the assembled cannula and reducer subassemblies according to a third embodiment of the invention.
Figure 8A:
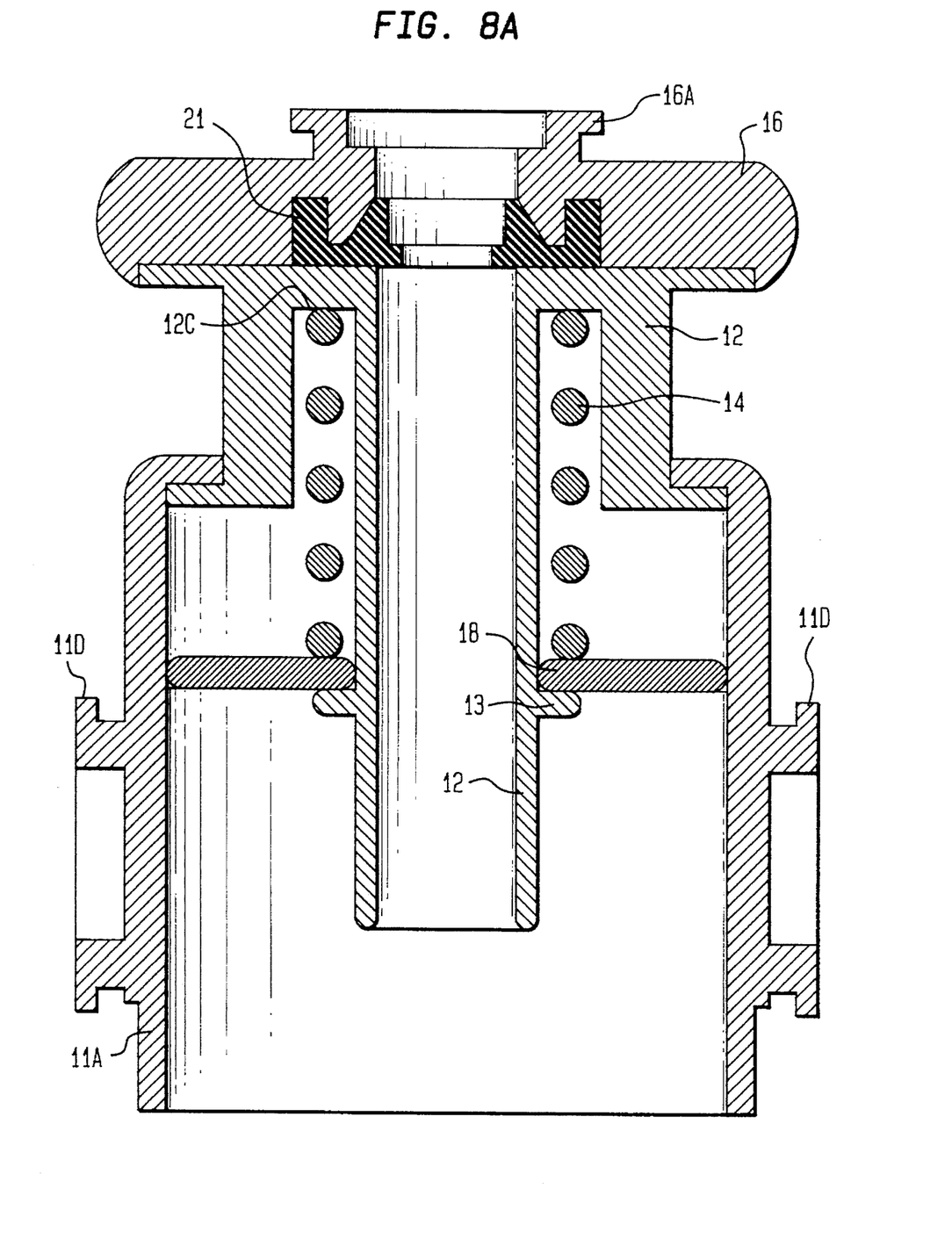
FIG. 8A is a cross-sectional illustration of the reducer subassembly of the preferred embodiment illustrated in FIGS. 1, 4, 4A, and 4B.
Figure 8B:
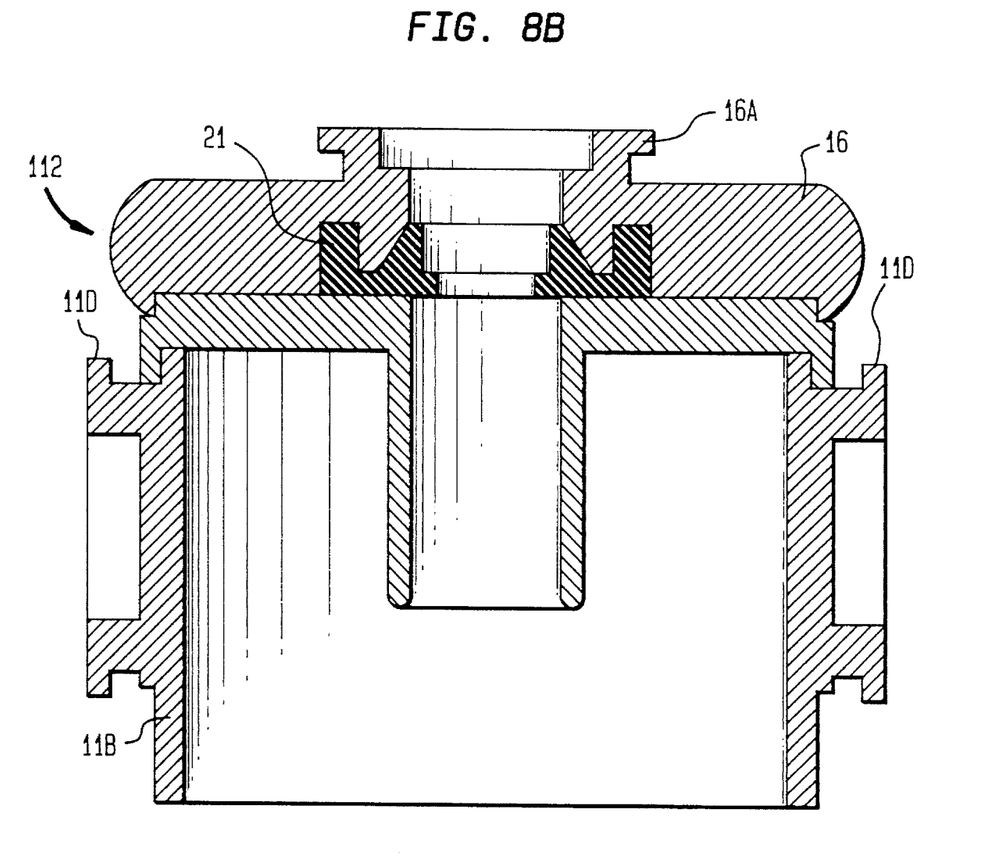
FIG. 8B is a cross-sectional illustration of the reducer subassembly of the second embodiment illustrated in FIGS. 2 and 5.
Figure 8C:
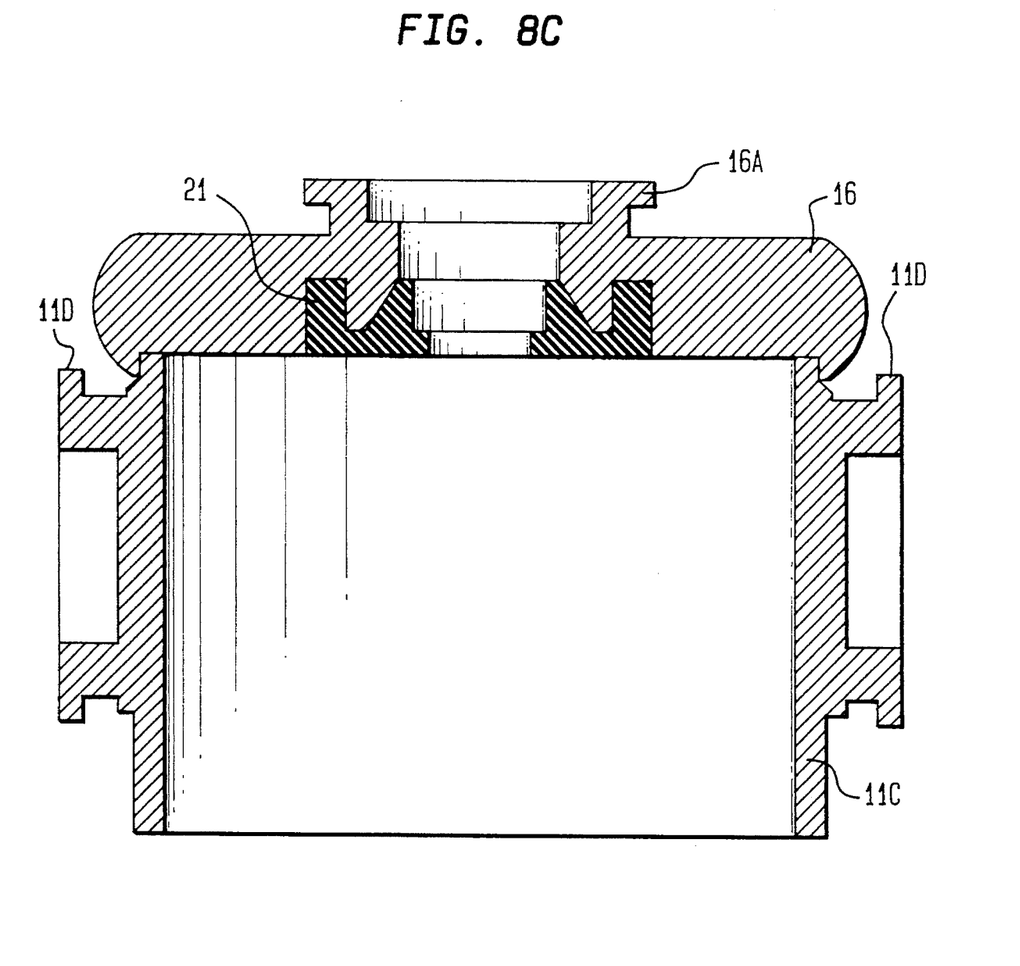
FIG. 8C is a cross-sectional illustration of the reducer subassembly of the third embodiment illustrated in FIGS. 3 and 6.
Figure 10:
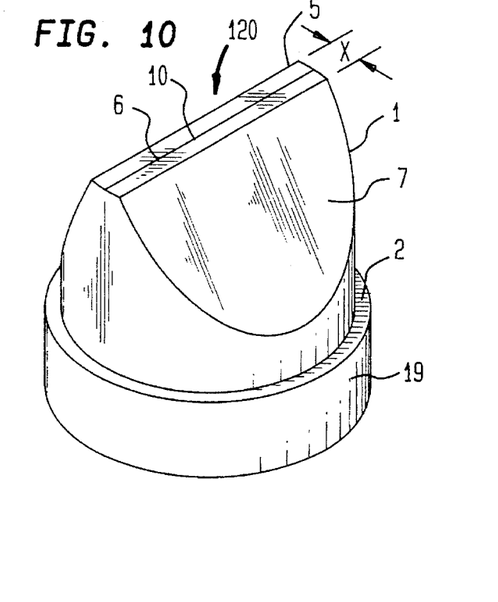
FIG. 10 is a side perspective view of the converging lip valve seal in the normally closed position.

The invention comprises a converging lip valve seal 120 illustrated in FIG. 10 and three embodiments of the apparatus illustrated in FIGS. 1, 2, and 3 that enhance its use and effectiveness. According to the preferred embodiment 110 illustrated in FIGS. 1, 4, 4A, 4B and 8A, the dual operational, converging lip valve seal opening means, 12, either automatic (FIG. 4A) or manual (FIG. 4B), is incorporated with the same modular components in a second embodiment 112 illustrated in FIGS. 2, 5 and 8B and a third embodiment 114 illustrated in FIGS. 3, 6 and 8C.

Figure 12:
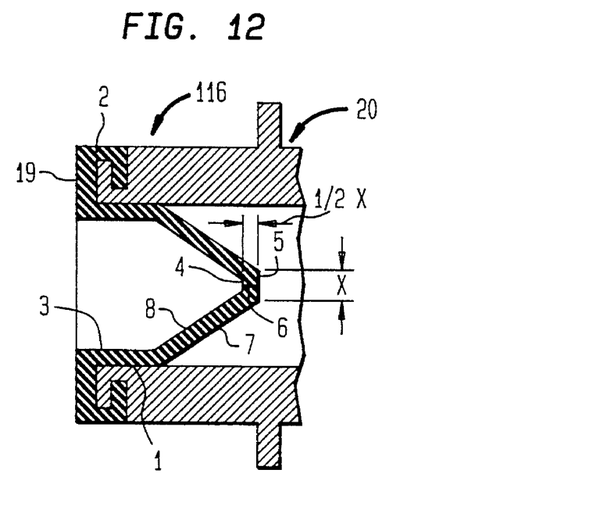
FIG. 12 is a cross-sectional illustration of the converging lip valve seal illustrating the two internal and external lip edges of the valve seal.

FIG. 10 illustrates the converging lip valve 120 in a normally closed position. The valve or valve seal 120 is preferably made of a flexible, resilient material having a high resistance to cutting or tearing as well as high lubricity characteristics such as synthetic polyisopilene or a medical grade silicone. As illustrated in FIGS. 10 and 12, the converging lip valve 120 is comprised of a cylindrical body 1 which fits axially into the bore of cannula housing 20 in a slight press fit. Interlocking means 2 fits into corresponding recesses in the cannula housing 20, restricting axial movement during use and providing for easy removal for replacement with a reusable cannula. The inner lumen 3 begins as a circular shape parallel to the central axis for a distance to provide a large pathway for easy access by irregular and sharp instruments. Thereafter, it tapers to a "V-chisel" cross section 8 converging inward to a truncated flat surface 4 of exterior width "X" perpendicular to the central axis at the distal end. The opposing lips have a thickness "½ X". The flat external leading surface 5 has a width "X" perpendicular to the central axis of the cannula 31 and parallel to surface 4. A slit 6 creates a first set of individually sealable internal converging valve lip edges 9 located on internal surface 4 and oppositely a second set of external valve lip edges 10 on surface 5 that are maintained closed when gas pressure exerts force on walls 7. Walls 7 are truncated and run parallel and opposite to internal surface 8 and are of the same thickness "½ X" as surfaces 4 and 5.

Figure 13:
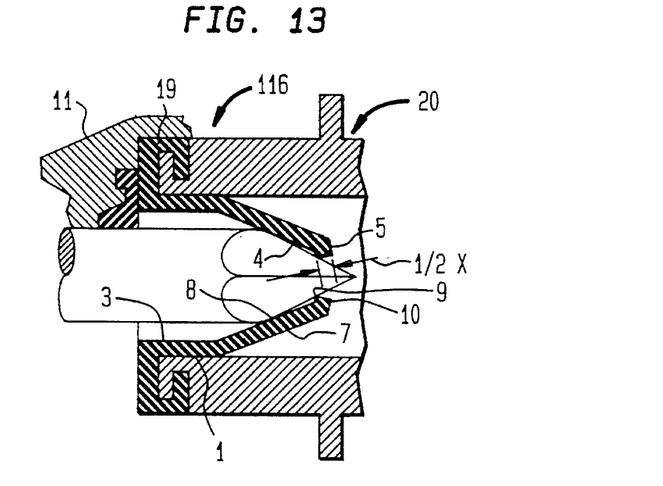
FIG. 13 is a cross-sectional illustration of the converging lip valve seal illustrating the deformation of valve lips as a sharp trocar is passed through the valve seal.
Figure 14:
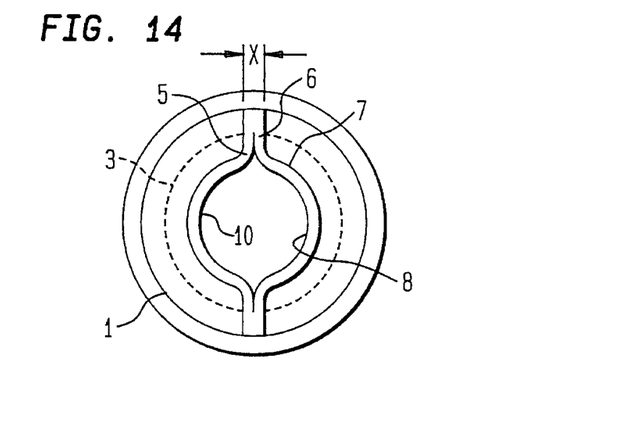
FIG. 14 is a front view of the converging lip valve seal illustrating the valve lips in the full opened position.

FIG. 13 illustrates in cross section the "V-chisel" and perpendicular wall shape that provides stiffness and a pathway for sharp devices to pass freely through slit 6. The first set of internal lip edges 9 absorb cuts or tears. The external surface 5 with external lip edges 10 moves outward such that contact cannot be made by sharp edges due to thickness "½ X". Therefore, the external lip edges 10 of surface 5 are protected from cuts thereby ensuring a consistent leak-proof closure. The "V-chisel" cross section and wall thickness provide important stiffness by maintaining lips extended at their distal end.

Figure 11:
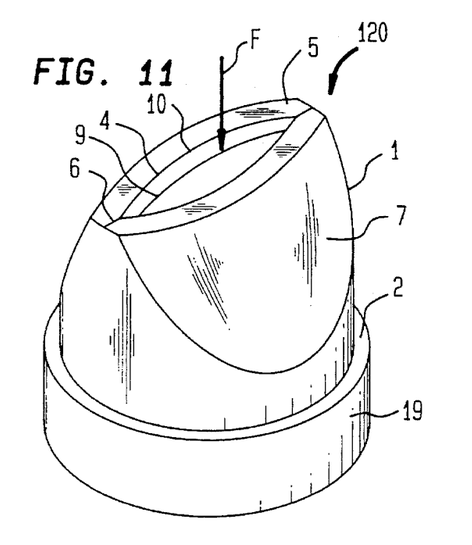
FIG. 11 is a side perspective view of the converging lip valve seal illustrating the application of a force F.

FIG. 11 illustrates how stiffness causes the cylindrical walls to bend inward creating an opening as the slit 6 expands, instead of folding inward when a force, indicated by the arrow F, is applied. Force F is experienced in the prior art when tissues and/or instruments are withdrawn from the abdominal cavity.

Figure 4:
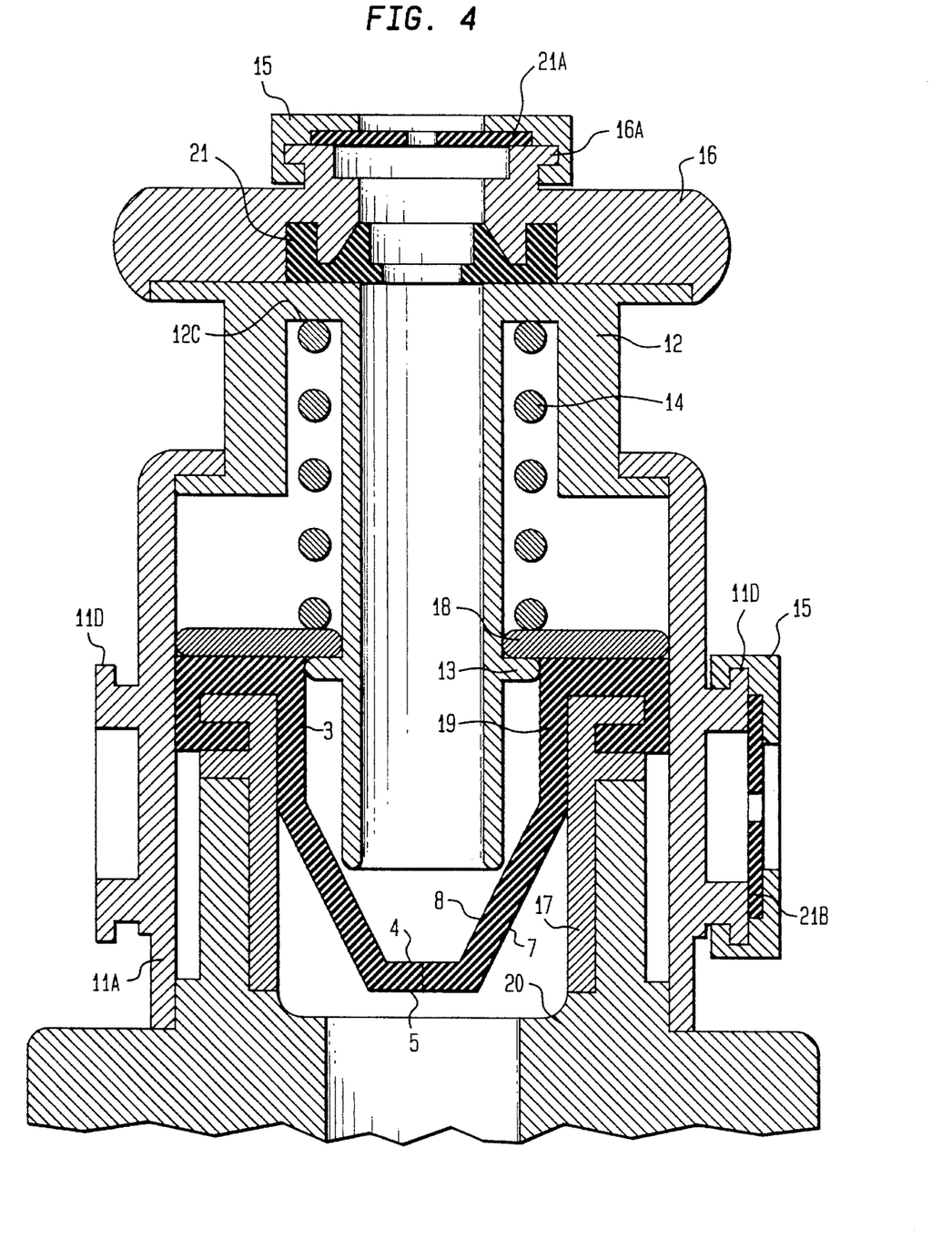
FIG. 4 is a cross-sectional illustration of the preferred embodiment of the invention as illustrated in FIG. 1.

The preferred embodiment 110 of the invention provides for a dual operation to open converging lip valve 19. There must be absolutely no resistance, when the operative procedure demands single-handed operation of instruments through the trocar. Also, when special instruments are used, because of their irregular shape and sharpness, such as articulated stapling devices, it is important that they do not catch on the lips of the valve. If they do catch, they can be difficult to remove and can possibly create a tear in the valve. In the preferred embodiment 110 illustrated in FIGS. 1, 4, 4A, 4B, and 8A, a slidable tubular structure 12, is located concentrically within the reducer subassembly 11A. A slidable retainer 17 in which the converging lip valve 19 is contained, is located in the cannula housing 20. A spring means 14 surrounds the tubular structure 12 and is held between a recess 12C provided at its proximal end, and a slidable disc 18 at its distal end. Disc 18 is contained in the recess by a retention means 13 which is part of the tubular structure 12. Spring 14 acts to bias the two slidable structures away from each other. The disc 18 slides along tubular structure 12. The converging lip valve 19 and retaining means 17 are slidable within cannula housing 20 and the tubular structure 12 is slidable within reducer subassembly 11A. Reducer subassembly 11A, when assembled with cannula housing 20, as shown in FIG. 4, is such that the tubular structure 12 is located just short of contact with the internal wall 8 of valve 19 such that the lip edges located on surfaces 4 and 5 are closed and no gas is allowed to pass outward from the abdominal cavity. A fixed or permanent second seal 21 is located concentrically within tubular structure 12. An interchangeable end seal attachment mechanism 15 containing a downsized interchangeable seal 21A can accommodate the use of a smaller instrument with a smaller outside diameter. The smaller outside diameter instrument can be sealed by fixed or permanent seal 21 and is shown attached to reducer subassembly 11A via attachment structure 16A.

Figure 4A:
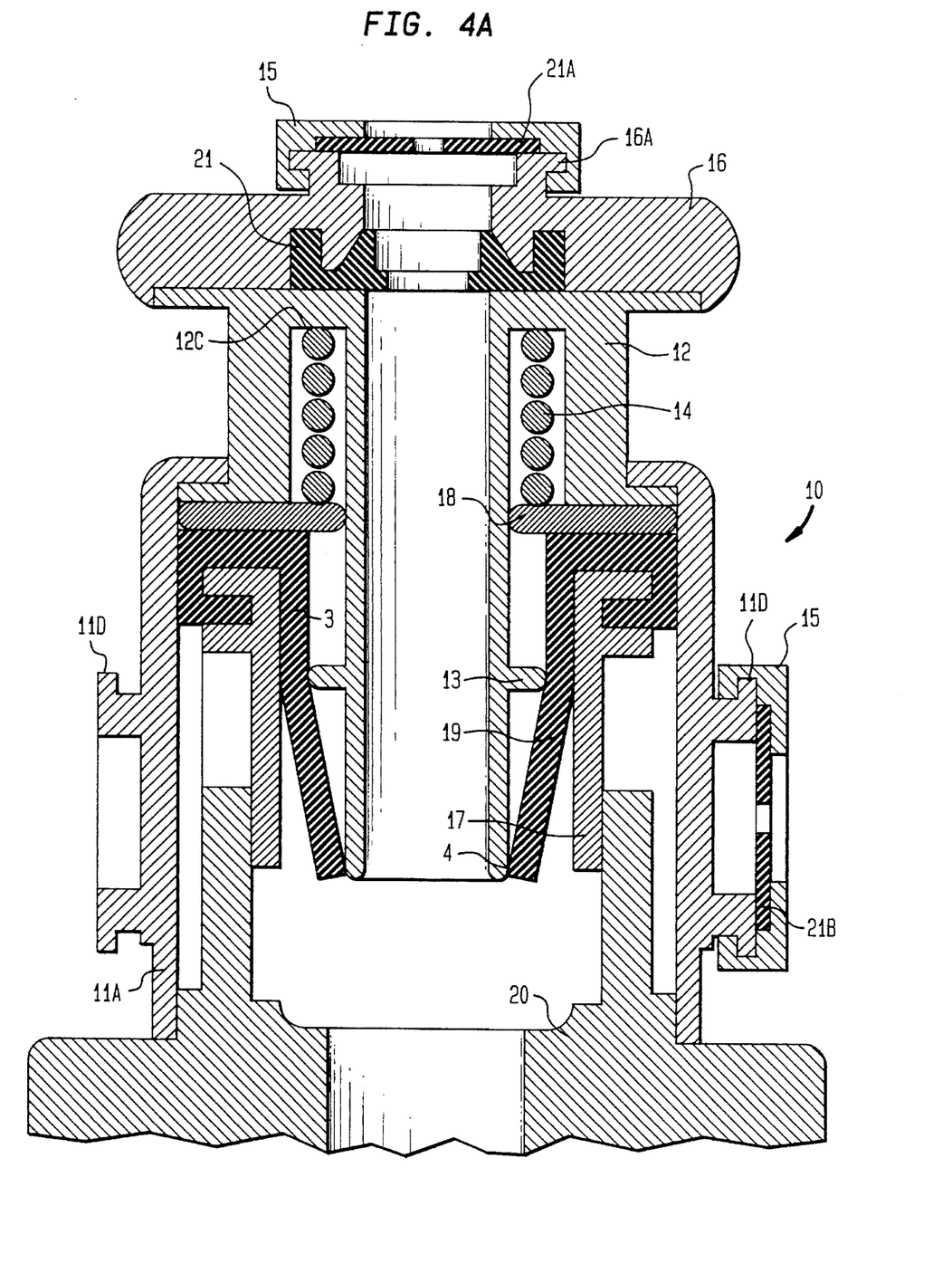
FIG. 4A is a cross-sectional illustration of the preferred embodiment illustrated in FIG. 1 with the valve in an automatically opened position.

During an operative procedure, force from withdrawal of tissue and irregular shaped instruments is exerted by the converging lip valve edges 5. The converging lip valve 19 and retention means 17 in which it is contained, will move outward and spring 14 will be compressed by movement of disc 18. The valve lips 4 and 5 will then pass over tubular structure 12 thereby opening valve 19 as shown in FIG. 4A. The tubular structure 12 then becomes the pathway to permit non-resisted withdrawal of tissue or instruments through the tube 12. When the force is removed and withdrawal of the instrument, such as a trocar, is completed, spring 14 returns to its original position. The valve 19 within valve retainer 17 also returns to its original position passing through valve lips 4 and 5 of the tubular structure 12. The valve then closes to seal the lumen.

Figure 4B:
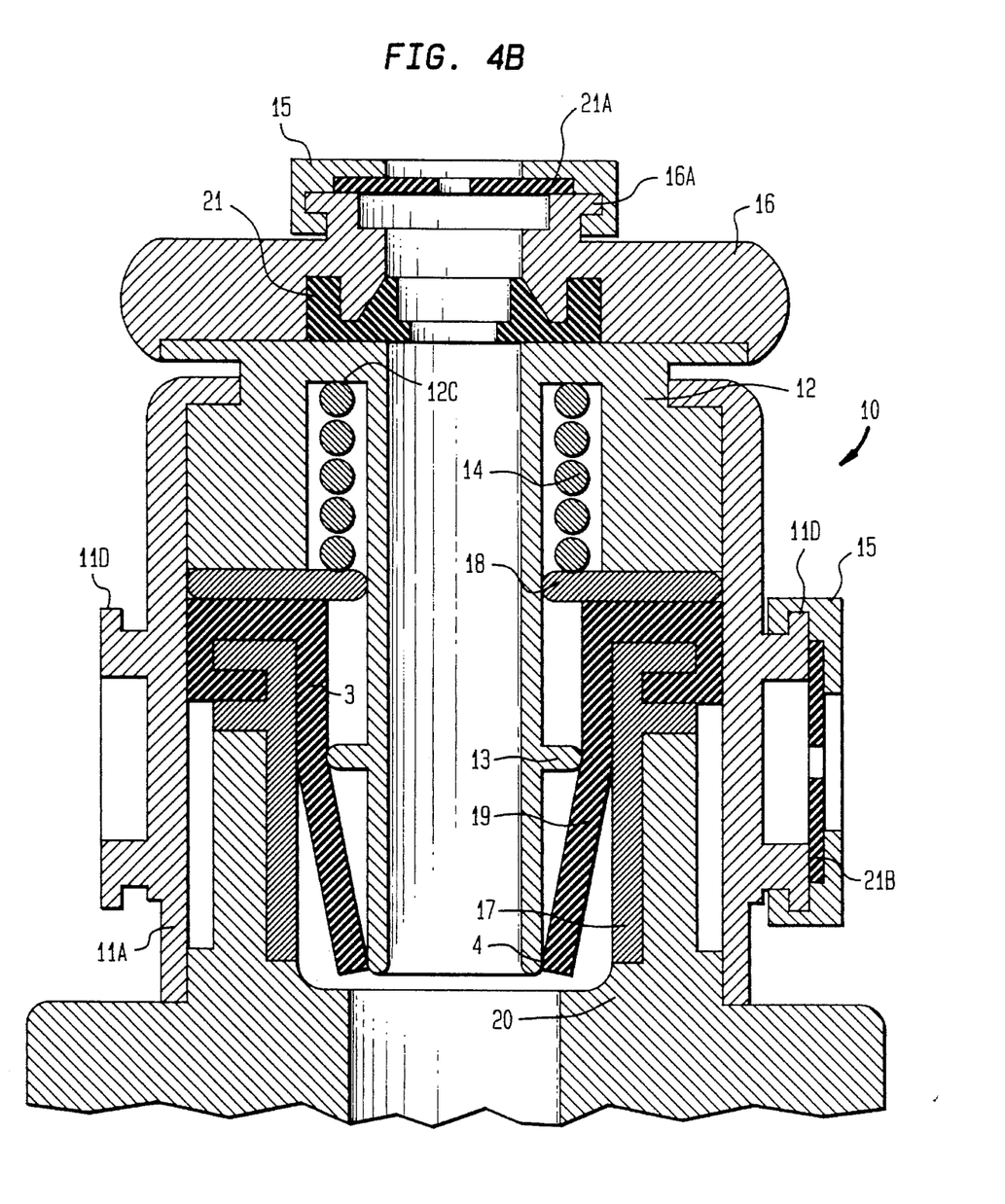
FIG. 4B is a cross-sectional illustration of the preferred embodiment illustrated in FIG. 1 with the valve in a manually opened position.

In certain procedures, when it is desirous to manually open the valve, this is accomplished by pushing the fixed seal subassembly 16 inward. The spring 14 compresses and the tubular structure 12 passes inwardly through the valve lip edges 9 and 10 of converging lip valve 19 as shown in FIG. 4B. The valve lips open such that they are removed from potential contact and a pathway within tubular structure 12 is created through which surgical instruments or tissue can readily pass without contact or damage to the valve 19. Release of spring 14 causes the tubular structure 12 to return to its outwardly biased original position and the valve lips 9 and 10 close and seal the lumen of the cannula.

Figure 5:
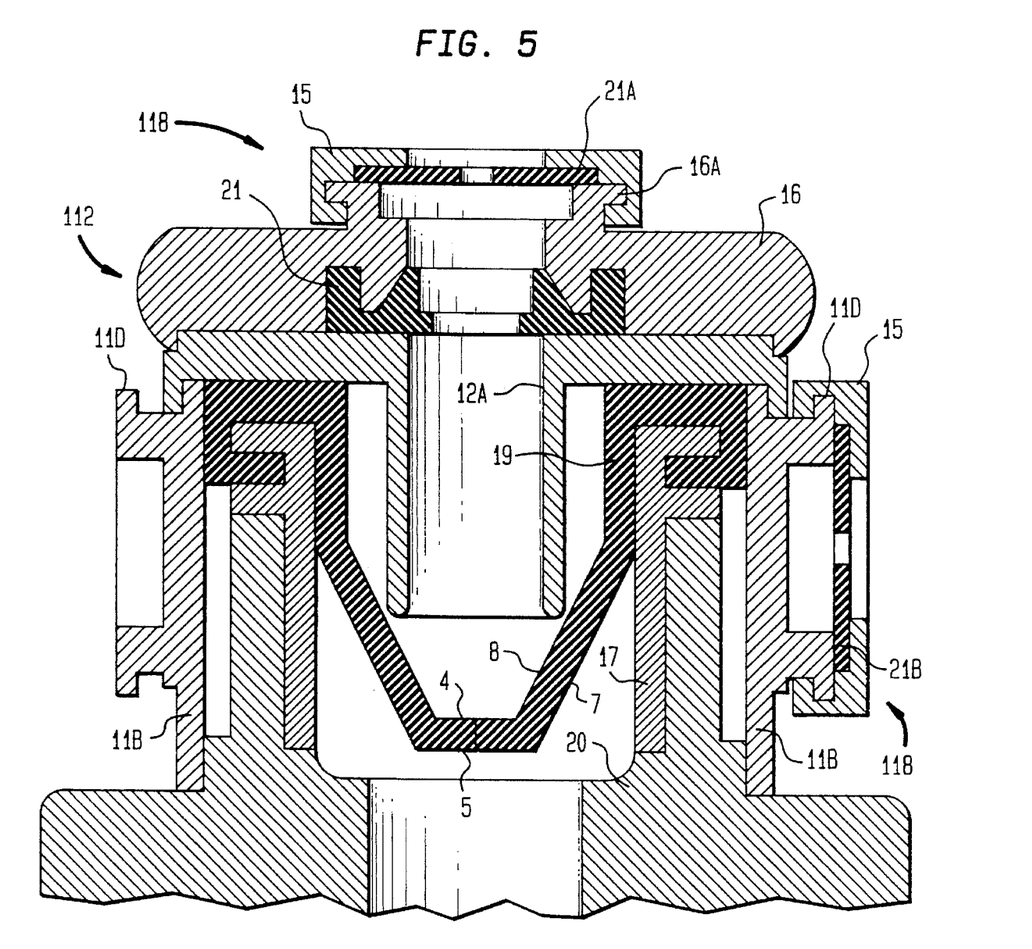
FIG. 5 is a cross-sectional illustration of the second alternative embodiment illustrated in FIG. 2.

FIGS. 2 and 5 illustrate a second embodiment 112 of the invention. It comprises a cannula housing 20, illustrated in FIG. 7, which is attachable and removable with respect to a reducer subassembly 11B, illustrated in FIG. 8B, which in turn is attachable and removable with respect to a reducer interchangeable second seal subassembly 15, illustrated in FIG. 9. A tubular structure 12A is located concentrically within reducer subassembly 11B. When assembled with cannula housing 20, the tubular structure 12A is positioned in a fixed relationship concentrically within converging lip valve 19 just short of making contact with internal walls 8. Therefore, when tissues and instruments are withdrawn from the cavity, any force felt by the valve lips 5 will not result in said lips folding inward. They can only move rearward a short distance until contact of inner walls 8 is made and support is provided by the tubular structure 12. The base of tubular structure 12 then becomes the exiting pathway for withdrawal for instruments and tissue thereby reducing the force of resistance to the withdrawn instruments or tissue. The tubular structure 12A located within subassembly 11B, as shown in FIG. 5, contains within its central bore, a fixed second seal subassembly 16. The seal subassembly 16 comprises a second seal means 21 and an attachment means 16A. A reducer interchangeable end seal subassembly 15 attached to subassembly 16 further includes an interchangeable end seal 21A.

Figure 6:
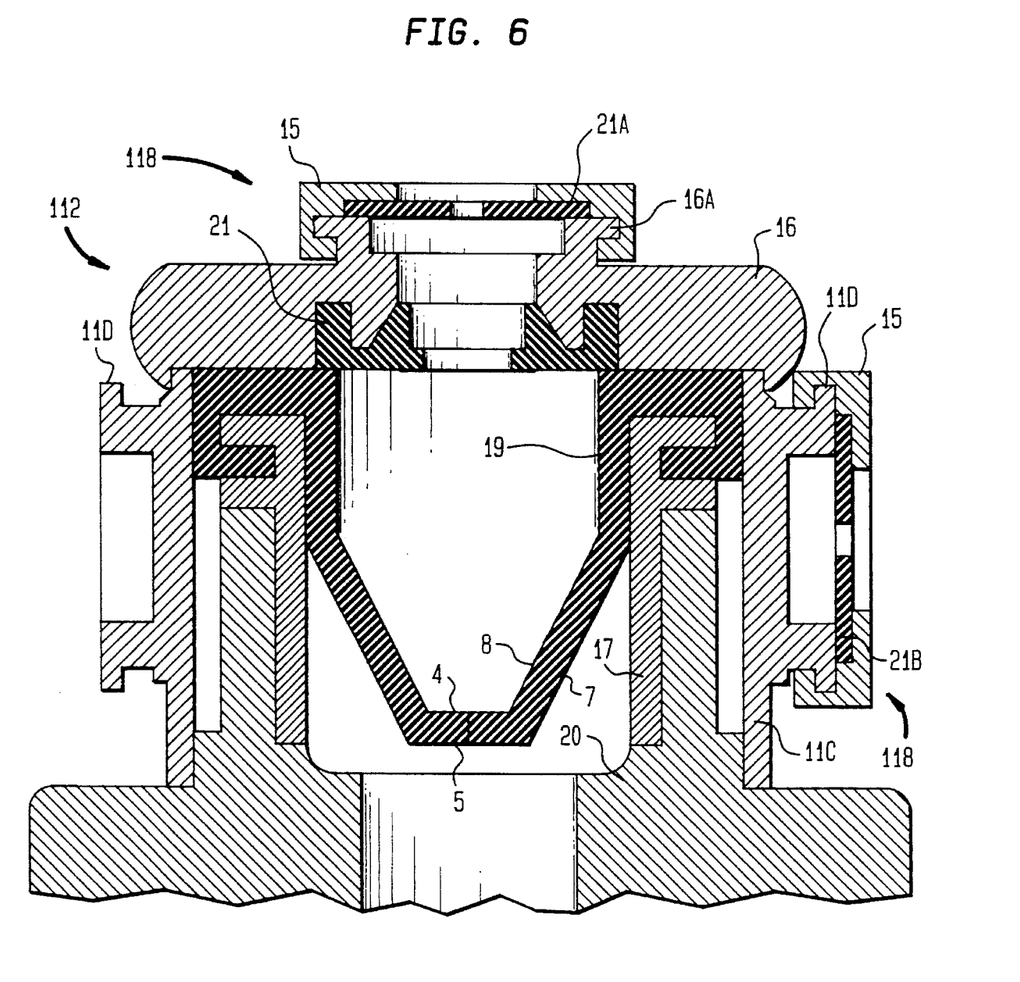
FIG. 6 is a cross-sectional illustration of the third alternative embodiment illustrated in FIG. 3.
Figure 7:
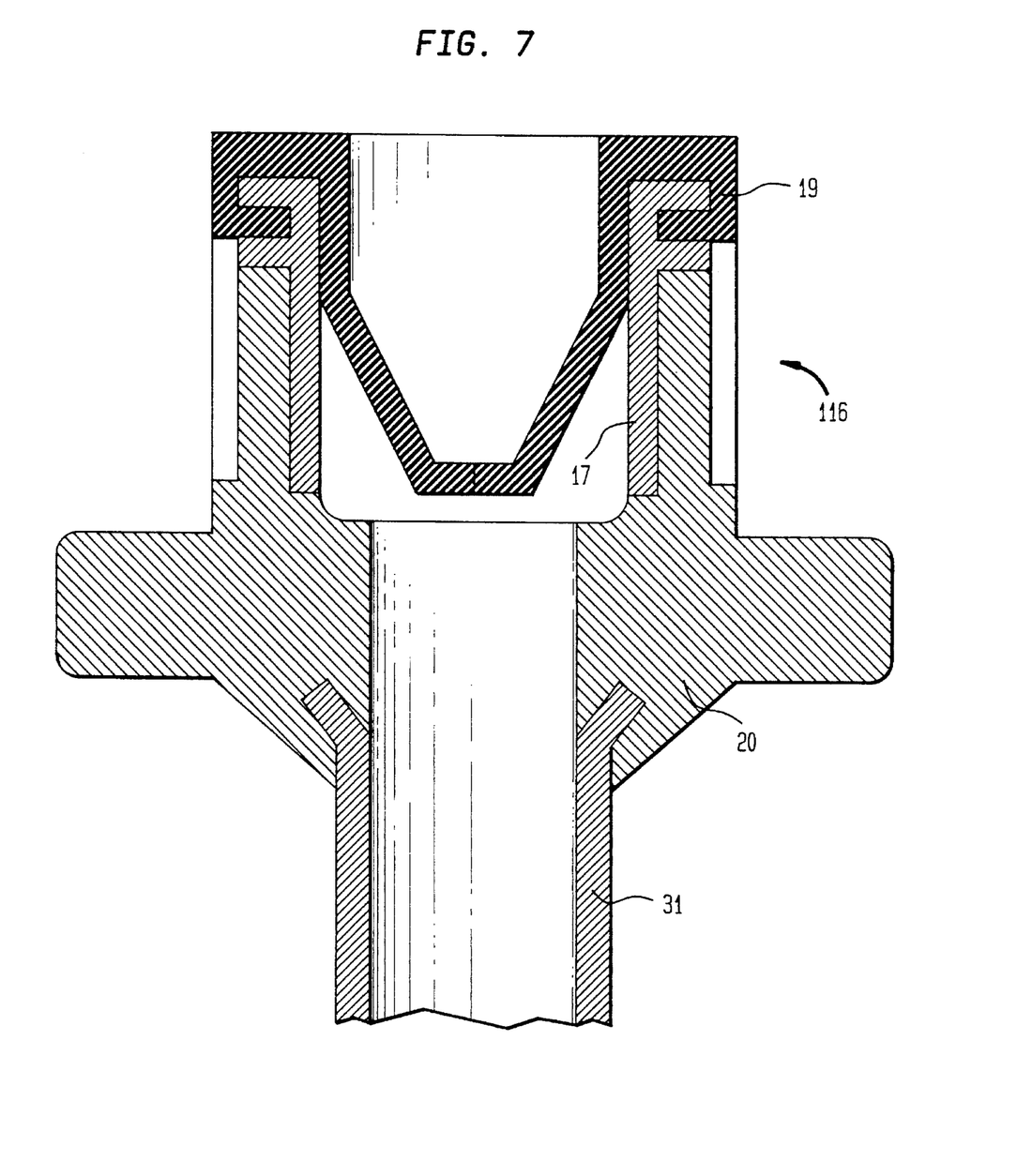
FIG. 7 is a cross-sectional illustration of the cannula subassembly of the embodiments illustrated in FIGS. 1, 2, and 3.
Figure 9:
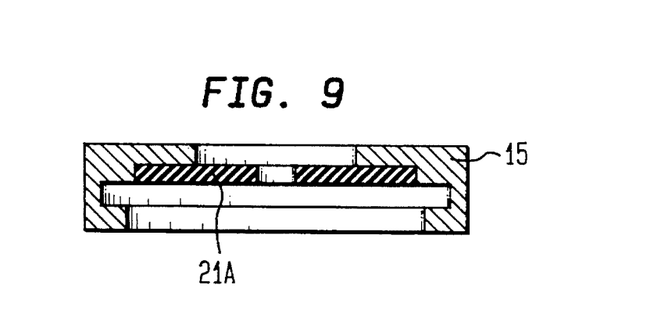
FIG. 9 is a cross-sectional illustration of the interchangeable second or permanent seal.

FIGS. 3 and 6 illustrate a third embodiment 114 of the invention. The third embodiment 114 comprises a cannula housing 20, such as illustrated in FIG. 7, which is attachable and removable with respect to a reducer subassembly 11C, such as illustrated in FIG. 6, which is attachable and removable with respect to a reducer interchangeable second or end seal subassembly 15, such as illustrated in FIG. 9. Because the third embodiment 114 does not contain a valve opening mechanism, the converging lip valve 19 is preferably coated with a silicone lubricant to reduce frictional resistance. Reducer subassembly 11C contains within its central bore a fixed second seal subassembly 16 comprising second seal 21, and an attachment structure 16A, to which reducer interchangeable second seal subassembly 15 is attachable and which further includes an interchangeable end seal 21A.

In all of the foregoing embodiments of the invention, when varying interchangeable end seals 21A and 21B are required, they can be easily removed and exchanged for the right size. Reducer interchangeable seal subassembly 15 is attachable to seal subassembly 16 by seal subassembly grooves 16A and corresponding recesses in the reducer interchangeable seal 15. Grooves 16A in the tubular structure 12 of the preferred embodiment 110 are shown in FIGS. 1 and 4. In the second embodiment 112, they are shown in FIGS. 2 and 5. In the third embodiment 114, they are shown in FIGS. 3 and 6 as a component of the reducer subassembly 11C. In all three embodiments, after interchangeable second seals 21A, 21B, located within reducer interchangeable second seal subassembly 15 have been used and are no longer needed, the reducer interchangeable end seal subassembly 15 can be stored in a standby position by attaching the reducer interchangeable end seal subassembly 15 to corresponding attachment recesses 11D. Attachment recesses 11D are located along walls of reducer housing 11A, 11B, or 11C shown in FIGS. 8A, 8B, and 8C. Alternatively, they can be located on cannula housing 20 as shown in FIG. 1. This provides for the safe and accountable keeping of the seals for later reuse, or for the discarding of the seals when the procedure has been completed.

Although the embodiments illustrated in the drawings and described herein demonstrate several possible variations within the framework of the invention, it will be apparent to those skilled in the art that other alternate constructions or modifications may be made by one having ordinary skill in the art without necessarily departing from the spirit or scope of the invention as a whole.

I claim:

1. A surgical apparatus for introducing an instrument into a patient comprising:

a cannula having a long central axis, a first end, a second end and a lumen running therethrough;

a cannula housing removably attached to said cannula;

a first seal means located within said cannula housing for preventing the leakage of insufflation gas from said patient when said cannula is located in said patient, said first seal means including two opposed lips which contact each other across a slit located between them, wherein said first seal means has a normally closed state and an open state when an instrument is introduced into said lumen of said cannula, said two lips of said first seal means each including an internal and an external edge and a substantially flat intermediate section between said internal and external edges, wherein said internal and external edges of said substantially flat intermediate sections of said lips are in substantial contact with each other when said first seal means is in said closed state, said first seal means further including a distal end having a relatively flat external surface which is perpendicular to said long central axis of said cannula, said relatively flat surface having a width X, said first seal means having walls with a generally V-shaped cross-section and further including a proximal end and an inner and outer surface which define the sidewalls of said first seal means, said first seal means further including an internal, relatively flat surface extending between the inner edges of said lips and said sidewalls, wherein the distance between said internal and external edges of said two lips is approximately ½ X;

a reducer subassembly removably attached to said cannula housing, said reducer subassembly including an internal lumen; and, a hollow tubular means having an interior bore therethrough and located within the lumen of said reducer subassembly and concentrically aligned with the long central axis of said cannula, said tubular means having a first end located near the inner surface of said first seal means which restricts the inward movement and collapse of said lips of said first seal means when an instrument is withdrawn through the lumen of said cannula, wherein when an instrument passes through said lumen of said cannula it first comes into contact with the internal edge of said two lips which absorbs the trauma of said contact and parts thereby protecting said external edges so that said first seal means will form a substantially gas-leakproof seal after said instrument is removed.

2. A surgical apparatus for introducing an instrument into a patient comprising:

a cannula having a long central axis, a first end, a second end and a lumen running therethrough;

a cannula housing removably attached to said cannula;

a first seal means located within said cannula housing for preventing the leakage of insufflation gas from said patient when said cannula is located in said patient, said first seal means including two opposed lips which contact each other across a slit located between them, wherein said first seal means has a normally closed state and an open state when an instrument is introduced into said lumen of said cannula, said two lips of said first seal means each including an internal and an external edge and a substantially flat intermediate section between said internal and external edges, wherein said internal and external edges and said substantially flat intermediate sections of said lips are in substantial contact with each other when said first seal means is in said closed state, said first seal means including a distal end having a relatively flat external surface which is perpendicular to said long central axis of said cannula, said relatively flat external surface having a width X, said first seal means further having a generally V-shaped cross-section and further including a proximal end and an inner and outer surface which define the sidewalls of said first seal means, said first seal means further including a relatively flat internal surface extending from said internal edges of said lips to said internal sidewalls of said first seal means, wherein the distance between said internal and external edges of said two lips is approximately ½ X, and further wherein said first seal means is removably attached to said cannula housing;

a reducer subassembly attachable to said cannula housing, said reducer subassembly including an internal lumen and further comprising a hollow, movable tubular means having an internal bore therethrough and located within the lumen of said reducer subassembly and concentrically aligned with the long central axis of said cannula, and a spring means located within said reducer subassembly for normally biasing said tubular means away from said first seal means; and, a hollow tubular means having an internal bore therethrough and located within the lumen of said reducer subassembly and concentrically aligned with the long central axis of said cannula, said hollow tubular means having a first end located near the inner surface of said first seal means which restricts the inward movement and collapse of said lips of said first seal means when an instrument is withdrawn through the lumen of said cannula, wherein when an instrument passes through said lumen of said cannula it first comes into contact with the internal edge of said two lips which absorbs the trauma of said contact and parts thereby protecting said external edges so that said first seal means will form a substantially gas-leakproof seal after said instrument is removed and, wherein when force is applied to said tubular means against said bias of said spring means, the tubular means contacts the inner surface of said first seal means and opens said first seal means creating a pathway through said first seal means so that an instrument can pass through said hollow interior bore of said tubular means without contacting said first seal means and without interfering with removal of tissues through said cannula.

3. The apparatus of claim 2 further comprising:

a permanent second seal means located concentrically within the bore of said tubular means for preventing the leakage of gas from the abdominal cavity of said patient when an instrument is present in the bore of said tubular means.

4. The apparatus of claim 3 further comprising:

interchangeable seal attachment means connected to said tubular means, and, a plurality of interchangeable seal means each having an aperture therethrough of a different diameter, wherein instruments of different outside diameters can be introduced into said tubular means and can be selectively matched with an interchangeable seal having an aperture that seals and matches said outside diameter of said instrument.

5. The apparatus of claim 4 further comprising:

external seal storage means connected to and located on the exterior of said apparatus for storing one or more of said interchangeable seal means.

6. The apparatus of claim 2 further comprising: interchangeable secondary seal attachment means connected to said reducer subassembly and concentrically aligned with the long central axis of said cannula; and, a plurality of interchangeable secondary seal means each having an aperture therethrough of a different diameter, wherein instruments of different outside diameters can be introduced into said cannula and selectively matched with an interchangeable secondary seal having an aperture that seals and matches said outside diameter of said instrument.

7. The apparatus of claim 2 further comprising:

a silicone lubricant coating on at least said internal edge of said two lips of said first seal means.

8. The apparatus of claim 2 wherein the slit in said first seal means is openable between at least 3 mm to 12 mm, and, wherein instruments having an outside diameter in the range of 3 mm to 12 mm can pass through said first seal means without significant frictional resistance through said first seal means.

9. The apparatus of claim 2 wherein said instrument comprises a trocar.

10. A surgical apparatus for introducing an instrument into a patient comprising:

a cannula having a long central axis, a first end, a second end and a lumen running therethrough;

a cannula housing removably attached to said cannula;

a first seal means located within said cannula housing for preventing the leakage of insufflation gas from said patient when said cannula is located in said patient, said first seal means including two opposed lips which contact each other across a slit located between them, wherein said first seal means has a normally closed state and an open state when an instrument is introduced into said lumen of said cannula, the two lips of said first seal means each including an internal and an external edge and a substantially flat intermediate section between said internal and external edges, wherein said internal and external edges and said substantially flat intermediate sections of said lips are in substantial contact with each other when said first seal means is in said closed state, said first seal means including a distal end having a relatively flat external surface which is perpendicular to said long central axis of said cannula, said relatively flat external surface having a width X, said first seal means having a generally V-shaped cross-section and further including a proximal end and an inner and outer surface which define the sidewalls of said first seal means, said first seal means further including a relatively flat internal surface extending from said internal edges of said lips to said internal sidewalls of said first seal means, wherein the distance between the internal and external edges of said two lips is approximately ½ X;

a reducer subassembly removably attached to said cannula housing, said reducer subassembly including an internal lumen;

a hollow tubular means having an internal bore therethrough and located within the lumen of said subassembly and concentrically aligned with the long central axis of said cannula, said hollow tubular means having a first end located near the inner surface of said first seal which restricts the inward movement and collapse of said lips of said first seal means when an instrument is withdrawn through the lumen of said cannula; and, external seal storage means connected to and located on the exterior of said apparatus for storing one or more seal means, wherein when an instrument passes through said lumen of said cannula it first comes into contact with the internal edge of said two lips which absorbs the trauma of said contact and parts thereby protecting said external edges so that said first seal means will form a substantially gas-leakproof seal after said instrument is removed.

* * * * *